United States Patent [19]

Vértesy et al.

[11] Patent Number: 4,623,714

[45] Date of Patent: Nov. 18, 1986

[54] NOVEL POLYPEPTIDES WITH AN α-AMYLASE-INHIBITING ACTION, A PROCESS FOR THEIR PREPARATION, THEIR USE AND PHARMACEUTICAL PRODUCTS

[75] Inventors: László Vértesy; Dominique Tripier, both of Eppstein; Harald Ritzel, Mainz, all of Fed. Rep. of Germany

[73] Assignee: Hoechst Aktiengesellschaft, Fed. Rep. of Germany

[21] Appl. No.: 668,839

[22] Filed: Nov. 6, 1984

[30] Foreign Application Priority Data

Jan. 21, 1984 [DE] Fed. Rep. of Germany ....... 3402021

[51] Int. Cl.$^4$ .................................................. C07K 7/10
[52] U.S. Cl. .................................... 530/324; 530/317
[58] Field of Search ................. 260/112.5 R; 530/324, 530/317

[56] References Cited

FOREIGN PATENT DOCUMENTS 2716050 10/1978 Fed. Rep. of Germany .

OTHER PUBLICATIONS

L. Stryker, "Biochemistry", W. H. Freeman & Co., San Francisco (1972), pp. 13–16.
Bergley's Manual of Determinative Bacteriology, 8th edition, Williams & Williams Corp., Baltimore (1974), pp. 771, 773.
P. Y. Chou and G. D. Fasman, "Advances in Enzymology", vol. 47, John Wiley & Sons (1978), pp. 45–148.

*Primary Examiner*—Delbert R. Phillips
*Attorney, Agent, or Firm*—Finnegan, Henderson, Farabow, Garrett & Dunner

[57] ABSTRACT

Cyclic polypeptides of the formula I

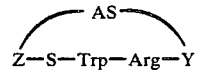

in which Z, S, Y and AS have the meanings given, a process for their preparation and their use are described. The compounds have an α-amylase-inhibiting action.

3 Claims, No Drawings

NOVEL POLYPEPTIDES WITH AN α-AMYLASE-INHIBITING ACTION, A PROCESS FOR THEIR PREPARATION, THEIR USE AND PHARMACEUTICAL PRODUCTS

The invention relates to novel biologically active cyclic polypeptides. They have α-amylase-inhibiting properties and can therefore be used in human medicine and veterinary medicine, in medical diagnostics and in the biotechnology of starch.

The polypeptides according to the invention consist of 10 to 200 amino acids and have the following formula I

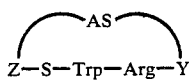

in which:
Z: denotes Gln, Asn or Met,
S: denotes Ser or Thr,
Y: denotes Phe, Tyr or Asn and
AS: denotes a polypeptide chain of 5 to 25 naturally occurring amino acids, which can in turn be substituted by further naturally occurring amino acids or peptide chains,
excluding the α-amylase inactivator Tendamistat (HOE 467) and the α-amylase inhibitor isolated from the culture filtrate of Streptomyces violaceoruber ATCC 31209.

The invention particularly relates to cyclic polypeptides of the formula I, in which Z denotes Gln, S denotes Ser, Y denotes Tyr and AS denotes a polypeptide chain of 12 amino acids, substituted by 2 peptide chains.

Of the polypeptides according to the invention, the peptide of the formula Ia

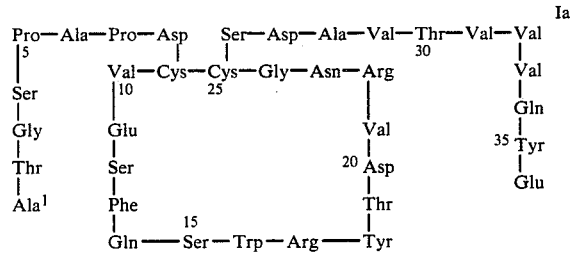

also designated AI-3688 below, and the following structural variants are preferred: the 1-dealanine derivative AI-3688a (the amino acid 1 is not Ala but Thr), the peptide AI-3688b, which differs from AI-3688 in that the 14th amino acid Gln has been replaced by Glu, the peptide AI-3688c, which differs from AI-3688 in that the 34th amino acid Gln has been replaced by Glu, the peptide AI-3688d, which differs from AI-3688a in that the 13th amino acid Gln has been replaced by Glu (this peptide is the 1-dealanine derivative of AI-3688b), the peptide AI-3688e, which differs from AI-3688a in that the 33rd amino acid Gln has been replaced by Glu (this peptide is the 1-dealanine derivative of AI-3688c), the peptide AI-3688f, which differs from AI-3688 in that both the 14th and the 34th amino acid Gln have been replaced by Glu, and the peptide AI-3688g, which is the 1-dealanine derivative of AI-3688f.

In these polypeptides, Z denotes Gln, S denotes Ser, Y denotes Tyr and AS denotes a polypeptide chain of 12 amino acids, which is disubstituted with 2 peptide chains of 8 or 7 and 11 amino acids. The peptides have 36 or 35 amino acids. The amino-terminal end of the amino acid sequence is on the alanine (1) or Thr. In the peptide AI-3688, there is a disulfide bridge between the Cys (9) and Cys (25). The disulfide bridges are at corresponding sites in the variants.

The amino acids contained in the inhibitor are described above and below by symbols, such as are used in the book by L. Stryer "Biochemistry", W. H. Freeman & Company, San Francisco, 1972, page 14 et seq.

The invention furthermore relates to a process for the preparation of the cyclic polypeptides of the formula I, pharmaceutical products containing a compound of the formula I, and the use as a medicament, diagnostic agent and reagent.

The invention particularly relates to processes for the preparation of the polypeptide AI-3688 and of variants AI-3688a to g, pharmaceutical products containing AI-3688 or one of the variants, and their use as a medicament, diagnostic agent and reagent.

The process for the preparation of the polypeptides of the formula I comprises culturing, in a fermentation medium by the submersion method, a Streptomycetes which produces polypeptides of the formula I, isolating the polypeptides from the mycelium or the culture filtrate in a manner which is known per se, and purifying it, Of the Streptomycetes, Streptomyces aureofaciens is particularly suitable.

AI-3688 and the structural variants AI-3688a–g are preferably obtained from the mycelium and culture filtrate of Streptomyces aureofaciens FH 1656. This strain has been deposited in the Deutsche Sammlung von Mikroorganismen (German Collection of Microorganisms (DSM) under registration number DSM 2790. However, the variants and mutants of this strain can also be used for obtaining AI-3688 and the structural variants.

The taxonomic characteristics of Streptomyces aureofaciens DSM 2790 correspond to the description of Streptomyces aureofaciens in Bergley's Manual of Determinative Bacteriology, 8th Edition, published by Williams & Wilkins Corp., Baltimore, 1974. The difference from the strains described lies in the metabolism product. Cyclic peptides have not hitherto been described as metabolism products of Streptomyces aureofaciens strains. Consequently, the strain is novel. The invention thus also relates to Streptomyces aureofaciens DSM 2790.

AI-3688 is advantageously isolated as follows:

Streptomyces aureofaciens DSM 2790 is cultured in an aqueous nutrient medium under submerse and preferably aerobic conditions, until a sufficient concentration of the AI-3688 is obtained. The nutrient medium contains on the one hand sources of carbon, such as, for example, carbohydrates, and on the other hand sources of nitrogen, which include suitable nitrogen compounds, such as, for example, protein-containing materials. Preferred compounds which supply carbon are glucose, sucrose, glycerol, malt extract, starch, oils, fats and the like. Examples of preferred substances which supply nitrogen are corn steep liquor, yeast extracts, soybean flour, fish meal, skimmed milk powder, partly digested casein or meat extract. So-called "synthetic" nutrient solutions can also be used. It may furthermore be useful to add trace elements, such as, for example, zinc, magnesium, iron, cobalt or manganese, to the fermentation medium.

The fermentation, which leads to the formation of the AI-3688, can be carried out within a wide temperature range. For example, it is carried out at temperatures between 10° and 40° C., preferably between about 25° and 35° C. The pH of the medium is likewise kept at values which promote the growth of the microorganisms, for example at values between 4.0 and 9.0, preferably between 5.0 and 8.0. The AI-3688 is usually formed in the culture solution after about 2–10 days, depending on the nutrient medium, such as, for example, its qualitative and quantitative composition, and the fermentation conditions, such as, for example, rate of aeration, temperature or pH value.

The AI-3688 is both in the mycelium and in the culture filtrate of the fermentation. Most of the AI-3688 is generally to be found in the culture filtrate. The aqueous phase is therefore advantageously separated from the mycelium, for example by filtration or centrifugation, and the AI-3688 is isolated from the particular phases by processes which are known per se and purified. A large number of processes are suitable for this, such as, for example, chromatography on ion exchangers, molecular sieves or adsorption resins, crystallization, solvent or salt precipitations, ultrafiltration, Craig partition and the like.

A preferred process for isolating the AI-3688 comprises adsorbing the inhibitor from the culture filtrate onto a suitable resin, such as, for example, a resin based on polystyrene, separating off this laden resin and isolating the inhibitor AI-3688 by elution with suitable buffer solutions, such as, for example, phosphate or bicarbonate buffer solution, or with optionally water-containing organic solvents, such as, for example, methanol, ethanol or acetone, but preferably with aqueous isopropanol. The inhibitor-containing eluates are concentrated by ultrafiltration in a known manner, desalination being carried out at the same time. The aqueous solution of the AI-3688 with a low ion content is then separated by chromatography on an ion exchanger column in a manner which is known per se. DEAE-cellulose or DEAE-modified cellulose (for example DEAE- ®Sephadex) is preferably used as the ion exchanger, but a large number of other commercially available cation and anion exchangers can also be used. The last step of the isolation is the use of a molecular sieve (for example ®Biogel P-6 or ®Sephadex). The resulting aqueous solutions of the pure material are then dried, for example by lyophilization. The specific activity is $1.5 \times 10^4$ α-amylase inhibitor units per mg of solid substance.

The pure inhibitor AI-3688 is a colorless polypeptide, amino acid analysis of which shows the presence of most naturally occurring amino acids. It has the abovementioned formula Ia.

During the fermentation, especially during prolonged fermentation, it may happen that the inhibitor AI-3688 is not a single substance. In these cases, the product can be separated into the individual components with the aid of the HPLC technique, preferably by means of HPLC on reversed phase RP 18 carriers with a water-/acetonitrile mixture (95:5) as the eluting agent. The components thus obtained have the above structures AI-3688 a, b, c, d, e, f and g. The structural variants are equally as effective as AI-3688.

A characteristic feature of AI-3688 and AI-3688 a to g is that the naturally occurring amino acids Met, Ile, Leu, Lys and His are missing.

Ultraviolet light is absorbed by AI-3688 in water with $\lambda_{max}=275$ nm, $E\ ^{1\%}1$ cm$=21$. The isoelectric point—determined by isoelectric focussing—is 4.2. The inhibitor AI-3688 is readily soluble in water and aqueous buffer solutions, the solubility decreasing only close to the isoelectric point.

AI-3688 and AI-3688 a–g differ from all the known α-amylase inhibitors in the abovementioned amino acid composition and of course in the structure, so that these are novel substances.

The chemical structure, as represented in formula Ia, shows the amino acid sequence of AI-3688 and moreover the presence of a ring formed by 17 amino acids by linking of the Cys (position 9) with the Cys (position 25). According to P. Y. Chou and G. D. Fasmann (Advances in Enzymology, Volume 47, pages 45–148, published by John Wiley & Son, 1978), conclusions as to the secondary structure of the peptides can be drawn from the primary structure—on the basis of the spatial peculiarities of the individual participating amino acids and their linkage, i.e. their sequence and their ring formation. A Chou/Fasmann analysis was carried out on the inhibitor AI-3688. It was found, surprisingly, that the part sequence of the ring: -Gln-Ser-Trp-Arg-Tyr- is incorporated in a suitable manner into the molecule at an exposed site i.e. spatially projecting, for biochemical reactions and is ultimately responsible for the activity. It has furthermore been found that by opening the ring containing 17 amino acids, for example by breaking the sulfur-sulfur bond of the cystin, a change is effected in the spatial structure, which means that the abovementioned decisive part sequence then no longer projects spatially and the enzyme-inhibiting activity is lost. Chemical derivatives of the α-amylase inhibitor AI-3688 formed by ring-opening are biologically and biochemically inactive (cf. Example 4). A characteristic of the α-amylase inactivators according to the invention which is essential for their inhibiting action is the presence of a large ring consisting of 10–30, preferably 17, amino acids and containing the amino acid sequence -Z-S-Trp-Arg-Y-, in particular -Gln-Ser-Trp-Arg-Tyr-. The composition of the part sequence as contained in the polypeptides according to the invention has little influence on the potency of the enzyme-inhibiting activity. The nature of the formation of the ring in the cyclic peptide is also not essential: neither the type of chemical bonding of the cyclization nor the route, i.e. whether obtained biologically or synthetically, is of importance for the activity, the presence of a ring system containing the given amino acid part sequences being important.

Investigations with the α-amylase inactivator isolated from *Streptomyces violaceoruber* ATCC 31209 and described in German Offenlegungsschrift No. 2,716,050 have shown that the above part sequence and the presence of a ring system are responsible for the inhibiting action. The investigation was carried out as follows.

Determination of the part sequence of the α-amylase inhibitor obtained from *Streptomyces violaceoruber* ATCC 31209: the sequencing of the α-amylase activator linearized by reductive or oxidative ring-opening was carried out with a Beckmann Sequenator ® in a 0.2 molar buffer system (Quadrol ®) automatically, using the amino acid phenylthiohydantoin (PTH) method. The following part sequence, inter alia, was found between the two cystein radicals of the substance: -Tyr-Phe-Gln-Ser-Trp-Arg-Tyr-Thr-Asp-Val-His-.

The properties of the inhibitors according to the invention are of interest in respect of the use as a therapeutic agent for diabetes and prediabetes as well as adiposity, and for supplementing the diet. On the basis of their properties, they are also useful as a reagent for diagnostic purposes.

Foodstuffs and confectionery containing starch lead to an increase in the blood sugar in humans and animals, and hence also to an increased secretion of insulin by the pancreas. Hyperglycemia arises as a result of cleavage of the starch in the digestive tract by the action of amylase and maltase to give glucose.

Hyperglycemia is particularly pronounced and long-lasting in diabetics.

Alimentary hyperglycemia and hyperinsulinemia following starch intake can be reduced by the amylase inhibitors according to the invention, especially by AI-3688. This action is dose-dependent. The amylase inhibitors according to the invention can therefore be used as a therapeutic agent for diabetes, prediabetes and adiposity, and to supplement the diet. Administration, in particular at mealtimes, is advisable for this purpose. The dosage, which should be based on the weight of the patient and the individual requirement, is about 10–500 mg per dose, which is advantageously taken at every mealtime. In justified isolated cases, the dosage can, however, also be above or below these limits.

The amylase inhibitors according to the invention are particularly suitable for oral administration. They can be used as the pure substance or in the form of a pharmaceutical formulation, employing the usual auxiliaries and excipients. Combined use with other medicaments, such as hypoglycemic or lipid-lowering substances, may also be advantageous. Since higher molecular weight peptides cannot or cannot noticeably be absorbed as such from the digestive tract, no toxicologically unacceptable side effects are to be expected from the substances according to the invention. Because of the not unusual amino acid composition, any possible proteolytic cleavage products are also to be regarded as physiologically acceptable. Accordingly, no striking symptoms were to be recognized on oral administration, also of high doses, of the amylase inhibitor AI-3688 to experimental animals. To test the pharmacological action of the amylase inhibitor, male Wistar rats which had been fasted and weighed between 200 and 250 g received an oral administration of the inhibitor AI-3688 according to the invention at the same time as 2 g of starch per kg of body weight. The activity of the product was demonstrated by determining blood sugar concentrations in blood samples withdrawn before, during and after the administration of the α-amylase inhibitor.

Besides the regulation of blood glucose, the polypeptides according to the invention can also be used to inhibit salivary α-amylase. This enzyme effects digestion of starch in the mouth and the sugar thus formed promotes caries of the teeth. The compounds according to the invention can therefore be used for prevention or a reduction of the development of caries.

They can also be used as biochemical reagents and as diagnostic agents.

Amylase Test

One amylase inhibitor unit (AIU) is defined as the amount of inhibitor which is capable of inhibiting two amylase units (AU) to the extent of 50% under the test conditions. By international convention, one amylase unit is the amount of enzyme which splits $1\mu$ equivalent of glycosidic bonds in starch in one minute. The $\mu$ equivalents of glucosidic bonds split are determined as $\mu$ equivalents of reducing sugars photometrically using dinitrosalicylic acid. The data are calculated as $\mu$ moles of maltose, which are determined with the aid of a maltose calibration line.

The tests are carried out as follows:

α-Amylase from pig pancreas and the solutions to be tested are preincubated together in 1.0 ml of 20 mM phosphate buffer, pH 6.9, +10 mM NaCl for 10–20 minutes at 37° C. The enzymatic reaction is started by addition of 1.0 ml of soluble starch (0.25% strength in the stated buffer) according to Zulkowski. After exactly 10 minutes, the reaction is stopped with 2.0 ml of dinitrosalicylic acid color reagent (according to Boehringer Mannheim: Biochemica-Information II) and the mixture is heated in a boiling water bath for 5 minutes for color development. After cooling, the extinction is measured at 546 nm against the reagent blank. The 50% inhibition is determined graphically by means of probability plotting in comparison with the non-inhibited enzyme reaction, using various amounts of inhibitor.

EXAMPLE 1

To obtain AI-3688, the inoculum was cultured (culture of the microorganism)—as is usual in microbiological practice—from a freeze-dried spore of the organism *Streptomyces aureofaciens* FH 1656, DSM 2790, by single colony passage and with slant tubes. The mass-production of spores necessary for the fermentation was also carried out on a solid nutrient medium in Roux bottles.

Agar medium for the plate, slant tubes and Roux bottle:
  dextrin: 15.0 g/liter
  sucrose: 3.0 g/liter
  meat extract: 1.0 g/liter
  yeast extract: 2.0 g/liter
  sodium chloride: 0.5 g/liter
  $K_2HPO_4$: 0.5 g/liter
  $FeSO_4$33 7 $H_2O$: 0.01 g/liter
  agar-agar: 2.0 g/liter
  pH value: 7.3
  Sterilization at 120° C. for 20 minutes.
  Incubation at 30° C. for 9 days.

A vegetative fermentation intermediate in a Fernbach flask (operating volume 1.2 liters) was inoculated with the spore suspension from the Roux bottle in 100 ml of sterile water.

Intermediate medium:
  glucose: 30.0 g/liter
  soybean flour: 20.0 g/liter
  maize starch: 2.0 g/liter
  urea: 1.0 g/liter
  ammonium nitrate: 1.0 g/liter
  malt extract: 5.0 g/liter
  pH value: 6.8
  Sterilization at 120° C. for 20 minutes.
  Incubation at 28° C. for 2 days on a shaking machine at 150 rpm with an amplitude of 5 cm.

Main fermentation:
  After preculture for 48 hours (see above), 200 liters of main fermentation medium were inoculated with 1.2 liters of inoculum from the Fernbach flask.

Medium:
  soluble starch: 4.0 g/liter
  glucose: 1.0 g/liter
  casein peptone: 1.0 g/liter
  corn steep (liquid): 0.4 g/liter
  soybean flour: 0.4 g/liter
  $(NH_4)_2HPO_4$: 0.8 g/liter
  pH value: 8.3
  Sterilization at 120° C. for 30 minutes.

The incubation was carried out for 5 days at 28° C. with stirring at a peripheral speed of 5 m/second and an aeration rate of 0.1 vvm. During the fermentation, the pH value fell and was controlled at 5.5–6.0 with sodium hydroxide. After 5 days, the product was harvested, the yield being 60 mg of AI-3688 per liter of culture solution.

EXAMPLE 2

180 liters of fermentation solution according to Example 1 were freed from the cell mass with the aid of a centrifuge and the clear liquid phase was brought to pH 4.9. The solution was then discharged onto a column containing 15 liters of polystyrene adsorption resin (Diaion ® HP-20), and the column was rinsed with 30 liters of water and eluted with water, to which increasing amounts of isopropanol had been added. The mixture containing 25% of isopropanol detached the inhibitor AI-3688 from the column. These active eluates (25 liters) were concentrated by ultrafiltration and desalinated, with addition of water and further ultrafiltration, until the residue no longer contained any detectable salts. The resulting concentrate (1.5 liters) was separated into its components on DEAE-modified cellulose (DEAE-Sephadex ®), which had been equilibrated with 1/15M phosphate buffer, pH 5.6. The α-amylase activity was eluted by applying an additional sodium chloride gradient. The corresponding fractions were desalinated. The product was concentrated in ultrafiltration cells (Amicon ®), which had been equilibrated with 1/15M phosphate buffer, pH 5.6. The α-amylase-inhibiting activity was eluted by applying an additional sodium chloride gradient. The corresponding fractions were desalinated. The product was concentrated again in ultrafiltration cells (Amicon ®). Final purification was carried out on polyacrylamide gel (Biogel P-6 ®), with pure water as the eluting agent. The AI-3688-containing fractions of this column were collected and freeze-dried. 1.2 g of a colorless powder with $1.5 \times 10^4$ α-amylase inhibitor units per mg resulted.

EXAMPLE 3

An AI-3688 inhibitor complex containing several components was obtained as described in Example 1, but the fermentation time stated in that example was extended from 5 days to 8 days. The fermentation solution was worked up according to Example 2, but the resulting colorless substance (0.9 g) was not chemically a single substance. 100 mg of this powder were dissolved in 1 ml of water/acetonitrile (95:5 v/v) and the solution was discharged onto a steel column (with internal dimensions of $3.2 \times 25$ cm$^2$) filled with reversed phase silica gel $RP_{18}$. The column was eluted with the solvent mixture water/acetonitrile (95:5), which had been brought to pH 2.1 with trifluoroacetic acid. Under an operating pressure of 70 bar, produced by reciprocating pumps, a flow rate of 8 ml per minute was established. The column outflow was monitored by determination of the ultraviolet absorption at 276 nm. After 41 to 43 minutes, several absorbing compounds were washed out of the column, and were all separately collected, tested for α-amylase-inhibiting action, concentrated in vacuo and then freeze-dried. The individual fractions were investigated for purity and their amino acid sequence determined using a Beckman Sequencer 890 C.

Analysis here of

Peak 1 showed an amino acid sequence which corresponded in structure to the formula Ia but in which the amino acid 34 (Glu) was replaced by Gln (=AI-3688c)

Peak 2 showed an amino acid sequence corresponding in structure to formula Ia (=AI-3688)

Peak 3 showed an amino acid sequence as described in formula Ia, but the amino acid 14 (Gln) was replaced by Glu (=AI-3688b)

Peak 4 showed 1-de-Ala-AI-3688 (=AI-3688a) and

Peak 5 showed a mixture of two 1-de-Ala-AI-3688 compounds; in one the amino acid 33 (Glu) was replaced by Gln (=AI-3688e), and in the other the amino acid 13 (Gln) was replaced by Glu (=AI-3688d).

The specific α-amylase-inhibiting activities of all the compounds were $(1.5 \pm 0.1) \times 10^4$ AIU per mg.

EXAMPLE 4

(Ring cleavage, detection of the active principle)

10 mg of AI-3688 according to Example 2 were dissolved in 5 ml of phosphate buffer, pH 7.0. A small sample was removed for testing, and 10 mg of dithioerythritol were than added. After the mixture had been left to stand at room temperature for 18 hours, the reaction solution was tested for α-amylase-inhibiting activity in comparison with the starting solution. Whilst the starting substance was completely active with $1.5 \times 10^4$ AIU per mg, the activity of the reaction solution was below the detection limit.

We claim:

1. A cyclic polypeptide selected from the group consisting of:

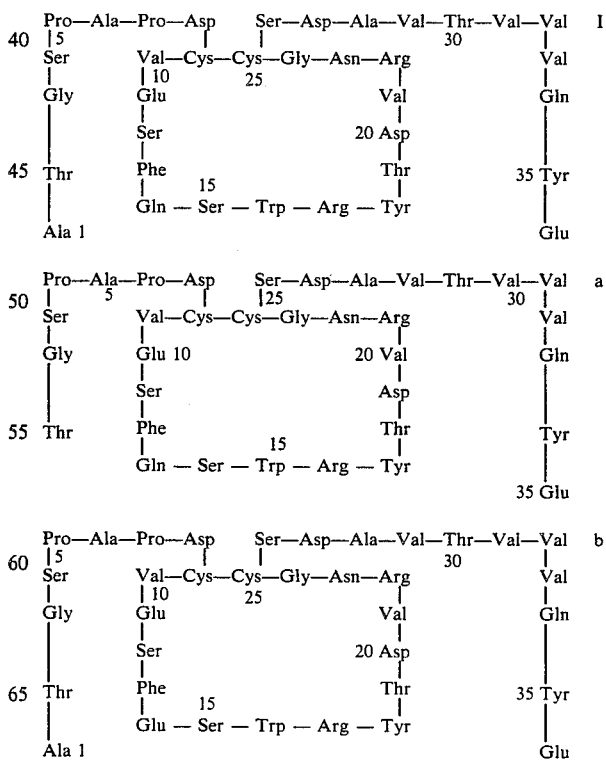

-continued

```
    Pro—Ala—Pro—Asp     Ser—Asp—Ala—Val—Thr—Val—Val           c
    |5              |   |                   30          |
    Ser             Val—Cys—Cys—Gly—Asn—Arg             Val
    |               |10      25                         |
    Gly             Glu                  Val            Glu
    |               |                    |
    |               Ser                 20 Asp
    |               |                    |
    Thr             Phe                  Thr            35 Tyr
    |               |    15               |             |
    |               Gln — Ser — Trp — Arg — Tyr
    Ala 1                                                Glu

Pro—Ala—Pro—Asp     Ser—Asp—Ala—Val—Thr—Val—Val           d
    |    5          |   |25                  30         |
    Ser             Val—Cys—Cys—Gly—Asn—Arg             Val
    |               |                                   |
    Gly             Glu 10               20 Val         Gln
    |               |                    |
    |               Ser                  Asp
    |               |                    |
    Thr             Phe                  Thr            Tyr
    |               |    15              |
    |               Glu — Ser — Trp — Arg — Tyr
                                                        35 Glu

Pro—Ala—Pro—Asp     Ser—Asp—Ala—Val—Thr—Val—Val           e
    |    5          |   |25                  30         |
    Ser             Val—Cys—Cys—Gly—Asn—Arg             Val
    |               |                                   |
    Gly             Glu 10               20 Val         Glu
    |               |                    |
    |               Ser                  Asp
    |               |                    |
    Thr             Phe                  Thr            Tyr
    |               |    15              |
    |               Gln — Ser — Trp — Arg — Tyr
                                                        35 Glu

Pro—Ala—Pro—Asp     Ser—Asp—Ala—Val—Thr—Val—Val           f
    |5              |   |                   30         |
    Ser             Val—Cys—Cys—Gly—Asn—Arg             Val
    |               |10      25                         |
    Gly             Glu                  Val            Glu
    |               |                    |
    |               Ser                 20 Asp
    |               |                    |
    Thr             Phe                  Thr            35 Tyr
    |               |    15               |             |
    |               Glu — Ser — Trp — Arg — Tyr
    Ala 1                                                Glu

-continued
and

Pro—Ala—Pro—Asp     Ser—Asp—Ala—Val—Thr—Val—Val           g
    |    5          |   |25                  30         |
    Ser             Val—Cys—Cys—Gly—Asn—Arg             Val
    |               |                                   |
    Gly             Glu 10               20 Val         Glu
    |               |                    |
    |               Ser                  Asp
    |               |                    |
    Thr             Phe                  Thr            Tyr
    |               |    15              |
    |               Glu — Ser — Trp — Arg — Tyr
                                                        35 Glu
```

2. The cyclic polypeptide as claimed in claim 1, which has the formula Ia

```
    Pro—Ala—Pro—Asp     Ser—Asp—Ala—Val—Thr—Val—Val           Ia
    |5              |   |                   30         |
    |               Val—Cys—Cys—Gly—Asn—Arg             Val
    Ser             |10      25                         |
    |               Glu                                 Gln
    Gly             |                    Val            |
    |               |                                  35 Tyr
    Thr             Ser                 20 Asp          |
    |               |                    |              Glu
    Ala¹            Phe                  Thr
                    |    15              |
                    Gln ——— Ser — Trp — Arg ——— Tyr
```

3. A pharmaceutical preparation containing the polypeptide of formula Ia

```
    Pro—Ala—Pro—Asp     Ser—Asp—Ala—Val—Thr—Val—Val           Ia
    |5              |   |                   30         |
    |               Val—Cys—Cys—Gly—Asn—Arg             Val
    Ser             |10      25                         |
    |               Glu                                 Gln
    Gly             |                    Val            |
    |               |                                  35 Tyr
    Thr             Ser                 20 Asp          |
    |               |                    |              Glu
    Ala¹            Phe                  Thr
                    |    15              |
                    Gln ——— Ser — Trp — Arg ——— Tyr
```

* * * * *